(12) United States Patent
Van Den Broek et al.

(10) Patent No.: US 8,545,565 B2
(45) Date of Patent: Oct. 1, 2013

(54) PROSTHESIS COMPRISING A CORE OF A GEL MATERIAL WITH A WOVEN ENVELOPE AND A METHOD FOR PRODUCING THE SAME AND USE THEREOF

(75) Inventors: Peter Ronald Van Den Broek, Eindhoven (NL); Jacques Marie René Huyghe, Beerse (BE); Silvia Wognum, Amsterdam (NL); Gert Nijenbanning, Oldenzaal (NL)

(73) Assignee: Technische Universiteit Eindhoven, Eindhoven (NL)

( * ) Notice: Subject to any disclaimer, the term of this patent is extended or adjusted under 35 U.S.C. 154(b) by 47 days.

(21) Appl. No.: 13/054,615

(22) PCT Filed: Jul. 15, 2009

(86) PCT No.: PCT/NL2009/050435
§ 371 (c)(1),
(2), (4) Date: Mar. 10, 2011

(87) PCT Pub. No.: WO2010/008285
PCT Pub. Date: Jan. 21, 2010

(65) Prior Publication Data
US 2011/0160865 A1    Jun. 30, 2011

(30) Foreign Application Priority Data
Jul. 18, 2008  (NL) ..................................... 1035724

(51) Int. Cl.
*A61F 2/44* (2006.01)
*B23P 11/00* (2006.01)

(52) U.S. Cl.
USPC .......................................... 623/17.16; 29/428

(58) Field of Classification Search
USPC ................... 623/17.11–17.16, 908; 606/246; 29/248, 428
See application file for complete search history.

(56) References Cited

U.S. PATENT DOCUMENTS 5,192,326 A * 3/1993 Bao et al. .................... 623/17.12
5,824,093 A * 10/1998 Ray et al. .................... 623/17.16
7,291,172 B2 * 11/2007 Marissen ................... 623/17.12

(Continued)

FOREIGN PATENT DOCUMENTS

EP        0 353 936       2/1990
WO       2004/049980      6/2004

(Continued)

OTHER PUBLICATIONS

International Search Report for International Application No. PCT/NL2009/050435, dated Oct. 26, 2009.

(Continued)

*Primary Examiner* — Pedro Philogene
(74) *Attorney, Agent, or Firm* — Barnes & Thornburg LLP

(57) ABSTRACT

The present application relates to a prosthesis comprising a core of a gel material and a fiber envelope which surrounds the core. In addition, the present application relates to a method for producing the same. The object of the present application is to provide a prosthesis which is based on a material which combines a low shear stiffness with a high degree of toughness and good swelling properties. Another object of the present invention is to provide a prosthesis which is based on a material which exhibits excellent durability and wear resistance.

19 Claims, 2 Drawing Sheets

(56) References Cited

U.S. PATENT DOCUMENTS

| | | | |
|---|---|---|---|
| 7,806,934 B2 * | 10/2010 | Gontarz et al. | 623/17.11 |
| 7,896,920 B2 * | 3/2011 | Yuksel et al. | 623/17.16 |
| 2002/0026244 A1 | 2/2002 | Trieu | |
| 2002/0183848 A1 * | 12/2002 | Ray et al. | 623/17.12 |

FOREIGN PATENT DOCUMENTS

| | | | |
|---|---|---|---|
| WO | 2005/013863 | 2/2005 | |
| WO | 2007/087364 | 8/2007 | |
| WO | WO2007/087364 * | 8/2007 | 623/17.12 |

OTHER PUBLICATIONS

Written Opinion of the International Searching Authority for International Patent Application No. PCT/NL2009/050435 mailed Jul. 15, 2009.

* cited by examiner

PROSTHESIS COMPRISING A CORE OF A GEL MATERIAL WITH A WOVEN ENVELOPE AND A METHOD FOR PRODUCING THE SAME AND USE THEREOF

CROSS-REFERENCE TO RELATED APPLICATIONS

The present application claims the benefit of priority to International Patent Application No. PCT/NL2009/050435 filed 15 Jul. 2009, which further claims the benefit of priority to Dutch Patent Application No. 1035724 filed 18 Jul. 2008, the contents of which are incorporated herein by reference in their entirety.

FIELD

The present invention relates to a prosthesis comprising a core of a gel material and a fibre envelope which surrounds the core. In addition, the present invention relates to a method for producing the same. The invention further relates to the uses of the prosthesis.

BACKGROUND

The natural intervertebral disc (discus intervertebralis or discus) forms part of a motion segment of the back. Such a motion segment consists of two vertebrae, an intervertebral disc (a cartilaginous disc which connects the vertebrae), two small posterior joints (facet joints), ligaments and muscles. All these elements jointly determine the extent to which movement of the back is possible. The intervertebral disc thus forms part of the overall locomotor apparatus, in which all the elements work together. This unit of elements can only perform its function if all the elements remain intact or are repaired in case of damage. If the intervertebral disc is for example insufficiently capable of performing its function because it is damaged, this may lead to the small joints being overloaded, which in turn may cause damage to said joints. Timely replacement of a damaged or defective intervertebral disc, preferably by an artificial intervertebral disc having comparable characteristics, is of major importance, therefore.

A natural intervertebral disc is built up of a gelatinous core (nucleus pulposus), which is enclosed in a fibrous ring (annulus fibrosus) (White et al., Clinical biomechanics of the spine, J.B. Lippencott Company, Philadelphia, 1978). The nucleus and the annulus both comprise stiff and mutually crosslinked collagen fibres, which are intertwined with proteoglycane chains. Said proteoglycane chains contain fixed, strongly negatively charged side chains (glycosamino glycanes), which interact with ions from the environment, as a result of which water is attracted by the intervertebral disc. Because of the high concentration of proteoglycane chains, the nucleus contains 85-95% water, whilst the annulus, which comprises a relatively great deal of collagen fibres and less proteoglyclane chains, contains 70-85% water. As a result of this specific composition, the disc allows movement of the vertebrae relative to each other and, in addition, has a shock-absorbing function. The two adjacent vertebrae comprise end plates consisting of hyaline ("vitreous") cartilage, which serves as a transition zone between the soft intervertebral disc and the hard vertebrae.

In case of back complaints associated with degeneration of the intervertebral disc, such as a serious hernia nucleus pulposus, surgery may be necessary. In some cases part of the intervertebral disc—generally the annulus—can be saved, but in serious cases the intervertebral disc must be replaced in its entirety. To restore the function of the vertebral column, a prosthesis must be implanted, which prosthesis takes over the mechanical function of the natural intervertebral disc, both as regards mechanical stiffness and as regards swelling behaviour.

Prostheses for intervertebral discs must meet a number of requirements (Eijkelkamp et al., The International Journal of Artificial Organs, 2001, 21 (5), 311-321) such as, inter ails, a correct geometry for an optimum attachment and an optimum pressure distribution in relation to the adjacent vertebrae. Further requirements include a sufficient degree of stiffness so as to obtain a good shock absorption, and a swelling behaviour comparable to that of the natural intervertebral disc.

U.S. Pat. No. 5,824,093 discloses a nucleus prosthesis (10) comprising a core of a gel material (12) and a woven fibre envelope (14).

WO 2005/013863 (present inventors) discloses a prosthesis comprising a core of a gel material (2) and a wrapped fibre envelope surrounding said core (3).

US 2002/026244 discloses a nucleus prosthesis comprising a core of hydrogel with a woven fibre envelope which surrounds the core.

EP 0 353 936 discloses a prosthesis comprising a core of a gel material with an envelope of a woven material.

U.S. Pat. No. 5,192,326 relates to a prosthesis comprising a core of a gel material enclosed by an envelope of a woven material.

International application WO 04/049980 relates to an artificial intervertebral disc comprising a core of a flexible material (silicone rubber) having the shape of a flattened body, with a lower and an upper side, which upper and lower side are connected by a lateral surface, around which core substantially radially oriented windings of a traction-resistant fibre have been applied.

A drawback of such an artificial intervertebral disc is that the windings of traction resistant fibres thus applied give the fibre structure insufficient shape stability and consequently allow only a limited buildup of swelling pressure in the core without loss of the original shape, which adversely affects the durability and strength of the artificial intervertebral disc. In other words, upon application of a substantial load the core material will bulge out between the windings of the fibres.

An example of a prosthesis for replacing intervertebral discs which was and/or is commercially available comprises a prosthesis based on a flexible core and rigid end plates, viz. a rubber core covered by titanium end plates (Acroflex®). Prostheses intended for replacing only the nucleus of an intervertebral disc, which prostheses are based on hydrogel materials, are known inter alia from U.S. Pat. Nos. 5,674,295; 6,402,784 and 5,047,055, in which the natural annulus is filled with a hydrogel material, which hydrogel material has swelling properties and which may or may not be surrounded by a membrane. Other prior art prostheses are so-called hinge prostheses, such as the Propisc II®, the Maverick® and the Charity® The drawback of such hinge prostheses is that wear occurs on the hinging parts. Prosthesis comprising a flexible core do not move via hinges but through deformation of the flexible core, which does not result in wear.

SUMMARY

It is an object of the present invention to provide a prosthesis for an intervertebral disc, which prosthesis imitates the characteristics of the natural intervertebral disc. Examples of characteristics, which will be explained in more detail hereinafter, include the swelling capacity of the prosthesis, osmotic bias, creep and relaxation, non-linear viscoelastic material behaviour, strength, stiffness, toughness and fatigue resistance.

Another object of the present invention is to provide a prosthesis which is based on a material which combines a low shear stiffness with a high degree of toughness, axial stiffness and durability.

Another object of the present invention is to provide a prosthesis which can be implanted in the human or animal body in a simple manner without any ligaments being seriously stretched near the location of the prosthesis upon surgical implantation of said prosthesis.

Another object of the present invention is to provide a prosthesis which exhibits a high degree of durability, a good shock absorption and good fatigue properties.

In addition to that it is an object of the present invention to provide a prosthesis for other joints and parts of joints in the body, such as a meniscus, for example.

One or more of the above objects are accomplished by the prosthesis as referred to in the introduction, which is characterised in that the fibre envelope consists of a woven material.

BRIEF DESCRIPTION OF THE FIGURES

The present invention will be explained in more detail hereinafter with reference to the following figures.

Figure 1:
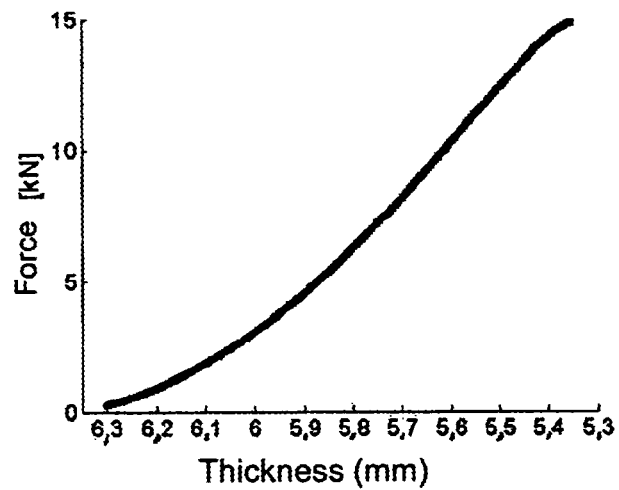
FIG. 1 shows of force-thickness diagram of the static loading of a sample prosthesis.

In this description of the present invention, the term "woven material" is understood to mean a material obtained by using techniques such as weaving, knitting, spool knitting, braiding knotting or bobbin-lacing and the like. This is in contrast to the prior art so-called wrapped envelope as described above.

The advantage of the present prosthesis, which advantage has been discovered by the inventors, is that the gel material of the core is correctly held in place in the core by the presence of a woven envelope, so that hardly any gel material will bulge out through the individual fibres of the envelope, in contrast to the situation that occurs when a wrapped envelope is used.

With prior art prostheses having a core consisting of a gel material surrounded by a thin membrane or a wrapped envelope, the gel material can bulge out or protrude through the membrane or the wrapped envelope under a load as occurs during normal use. When such a configuration is used, there is even a chance that when the prosthesis is subject to, for example, swelling pressure of the gel material or a load during use, the windings will shift relative to each other and over each other, as a result of which, as described above, openings are formed between the windings, through which openings the gel material bulges out. This is disadvantageous, because it adversely affects the structural integrity of the configuration and reduces the life, whilst gel material may be released, which can subsequently find its way into the body, possibly leading to undesirable side-effects for the patient.

A possible explanation—to which the present inventors do not wish to be confined—for the fact that the present prosthesis functions so well is that because of the use of a woven material the fibres, possibly in the form of threads or yarns, are arranged at relatively fixed positions relative to each other and major shifts relative to each other are thus not possible. In the case of a wrapped envelope, on the other hand, major shifts of the fibres relative to each other are possible, so that large openings can form between the fibres, through which the gel material of the core can bulge out. When woven materials are used, the extent to which individual fibres can shift within the material is more confined, and thus no large openings will be formed and less gel material, or even practically no gel material at all, will bulge out.

Another advantage of the present prosthesis is that the woven envelope exhibits a good durability, as experimentally demonstrated by the present inventors and as will be explained hereinafter in the Examples.

Another advantage of the present invention is that effecting a bond between the bone near which the prosthesis is placed on the one hand and the prosthesis on the other hand is made easier. The word "bone" refers to, for example, the bone material of vertebrae.

An additional advantage of the use of a woven envelope over, for example, a wrapped envelope according to the prior art is that the structure of the woven envelope with open meshes makes the ingrowth of bone into the woven envelope possible, which leads to an excellent bond with the adjacent bone material after implantation of the prosthesis into the body. Such ingrowth is less readily possible when wrapped envelopes are used.

An implanted prior art prosthesis comprising a wrapped envelope has a smoother surface than the present prosthesis, which comprises a woven envelope, because the latter comprises "junctions" or intersections of fibres, yarns and/or threads. Since the surface of the present prosthesis is less smooth, less migration will occur in the body due to the increased friction between the envelope of the prosthesis and the adjacent bone material.

The bulging out of core material can also be prevented by selecting a different core material, such as a silicone rubber, for example, as described in WO 04/049980. Such a configuration makes it virtually impossible to implant the prosthesis for an intervertebral disc without stretching the ligaments of the vertebrae, which is undesirable.

As already described before, a number of characteristics of the natural intervertebral disc are essential to the proper functioning thereof. Said characteristics will be briefly elucidated hereinafter.

The swelling capacity of the prosthesis is the ability of the prosthesis, and in particular the core of gel material, to swell as a result of the absorption of water. The swelling capacity can be adapted as desired by adapting the gel material in the core. If a hydrogel is used, the composition can be adapted so that the hydrogel will comprise more or fewer ionic compounds having a relatively higher or lower water-attracting capacity. The good swelling capacity of the present prosthesis makes it possible to surgically implant the prosthesis in reduced condition at the desired position in the body, so that ligaments present around the joint will not be overly stretched and damage can be prevented. Also removal of the prosthesis is possible in this way. An agent can be injected into the implanted prosthesis, for example by means of a syringe, causing the prosthesis to shrink/become smaller in the body, after which surgical removal will be less labourious.

According to the present invention, it is in particular preferable if the (hydro) gel can swell more than the dimension of the envelope allows. The stiffness of the prosthesis depends on the swelling pressure in the prosthesis, which is obtained by the balance between the swelling of the (hydro) gel and the stiffness of the woven envelope, as a result of which fibres are biased and the amount of swelling is limited. As a result of the internal pressure that is obtained in the gel, said gel will less easily exhibit tears.

In other words, without an envelope the (hydro) gel core could swell more than with an envelope; the envelope restricts the amount of swelling.

Osmotic bias of the prosthesis is obtained in that the core of gel material cannot swell further than allowed by the envelope, which leads to a bias in the core and interwoven envelope.

Creep is the time-dependent deformation at a constant load, as a result of which the stress level in the material decreases. When an intervertebral disc and also the present prosthesis is loaded, water will flow out, as a result of which the intervertebral disc will become thinner. When the load decreases, the thickness will increase again as a result of the inflow of water.

Stress relaxation (also called relaxation) is the decrease of the stress level in the material upon being subjected to a continuous mechanical load. An example of relaxation is the use of biased fibres, which are stretched and thus experience internal stress. After some time it will be found that the stress decreases whilst the amount of stretch remains unchanged. This is related to the viscoelastic behaviour of the material.

The inflow and outflow of water in a night and day rhythm, which rhythm is the result of the higher load during the day and the lower load during the night, result in stresses being spontaneously distributed over the prosthesis, the small joints and the ligaments, so that stress concentrations can be prevented.

Elastic materials directly exhibit stretch upon being loaded in tension and return to their original state when the load is released. Viscoelasticity is the property of materials that exhibit both viscous and elastic behaviour upon deformation. Viscoelastic materials exhibit time-dependent stretch. As a result of the viscous behaviour of the present prostheses, loads being exerted can be distributed more evenly over the prosthesis.

Non-linear viscoelastic behaviour means that in the case of a high stretch level the degree of stress per unit of stretch increases relatively more strongly than in the case of a low stress level. The stress-stretch relation is non-linear, therefore.

Strength provides information about the ability of the prosthesis to remain intact upon being subjected to a large force, and the toughness provides information about the ability of the prosthesis to remain intact upon undergoing major deformation.

Fatigue resistance is the resistance to fatigue, fatigue being the phenomenon that a material collapses under a varying, long-lasting load. The varying load may lead to breakage, even if the stresses remain far below the maximum flow or breaking stress at all locations. It is important that the present prostheses can perform its function for a long time after being implanted. A prosthesis for a joint part, such as an intervertebral disc, will be subjected to varying loads for a prolonged period of time, and it is of major importance, therefore, that the prosthesis exhibits a good resistance to fatigue. The fatigue resistance indicates the extent to which the prosthesis is resistant to a large number of loads, and thus what the useful life of the prosthesis will be.

The stiffness indicates the extent to which a material can exhibit deformation. The stiffer a material, the less deformation it will exhibit. The stiffness of the present prosthesis is obtained by the balance between the swelling capacity of in particular the core (as explained in the foregoing) on the one hand and the size and the stiffness of the envelope on the other hand. If a hydrogel material is used as the core material, the core can adapt itself upon being subjected to a load. After all, when a load is applied, water will be moved from the core to the environment, causing the stiffness to increase. Upon relaxation (no load being applied), the core will absorb water from the environment again as a result of the osmotic effect. The stiffness and the osmotic stress caused thereby protect the small joints in the motion segment against overload, because the load is born mainly by the prosthesis.

The degree of stiffness must be selected so that a compromise is found between the deformability of the joint on the one hand and the stability of said joint on the other hand; the implantation of a prosthesis must not interfere with said deformability and stability.

In the natural intervertebral disc the ratio between axial stiffness and shear stiffness of the prosthesis is about 1:8, whilst in a prosthesis comprising a flexible plastic core this ratio is about 1:3. The axial stiffness relates to the stiffness over the axis of the back. The shear stiffness relates to the stiffness caused by the extent to which lateral movement of vertebrae is possible.

During the movement of two vertebrae, the position of the axis of rotation or the rotation point changes, unlike hinged vertebrae having a fixed rotation point. The extent to which movement of the present prosthesis is possible is equal to that of the natural intervertebral disc.

It is preferable if the gel material according to the present invention is a hydrogel, i.e. that it consists partially or entirely of a hydrogel. The advantage of using a hydrogel is the excellent swelling capacity thereof.

It is in particular preferable to use an ionised hydrogel in the present prosthesis, viz. a hydrogel containing 0.02-2% ionised groups (amount of molequivalente charge per liter), preferably 0.05-1%, more preferably 0.1-0.5%, in particular 0.2-0.4%. An example of such a hydrogel is the combination of HEMA (hydroxyethyl methacrylate) and NaMA (sodium methacrylate), with preferably 0.1 to 20 wt. % NaMA, in particular 0.5 to 10 wt. % NaMa, more in particular 1 to 6 wt. % NaMA. NaMa contains negatively charged groups, whose action is comparable to that of the proteoglycane chains in a natural intervertebral disc, viz. attracting water. Other polymethacrylates may be used as well. The hydrogel material may further comprise additional components, such as water, crosslinkers, polymerisation initiating agents and other agents.

More in particular, the hydrogel that is used as the core material is reinforced with fibres so as to obtain a better durability, wear resistance and load properties of the present prosthesis.

A fibre-reinforced hydrogel material is known from "Composite hydrogels for implants": L. Ambrosio c.s. Proceedings of the institution of mechanical engineers, part H, Journal of Engineering in Medicine (1998), 212 (2), 93-9, Ref. 24. Bundles of polyethylene terephthalate fibres are used therein, which fibres are non-absorbent; these fibres are incorporated in the polymerised hydrogel. For a number of applications, the material obtained therewith is stiff in relation to the characteristic stiffness of soft biologic tissues it is intended to replace.

Young at al. (Biomaterials 1998, 19, 175-1752) describes a material based on poly-2-hydroxyethyl methacrylate (pHEMA) reinforced with Lycra fibres (with a low tensile strength). Fibre structures are provided in a hydrogel. The fibre-reinforced hydrogel contains about 1% fibre and can be used as artificial skin.

The prosthesis according to the present invention preferably comprises a fibre-reinforced hydrogel in the core material, the hydrogel being reinforced with fibres having a tensile strength of at most 1 GPa. Examples of such a fibre having a low tensile strength (also called elasticity modulus) are Lycra® or Spandex® having a stretch capacity in excess of 500%. Such fibres having a low tensile strength exhibit a good absorption of the hydrogel material and form a homogeneous mass, therefore. In addition, such fibres exhibit a good bond between the fibre and the hydrogel whilst reducing the risk of the hydrogel breaking out of the woven envelope.

In particular, the amount of fibres in the fibre-reinforced hydrogel is at least 5%, based on the weight of the hydrogel, so as to obtain an optimum balance between an adequate strength and durability of the prosthesis on the one hand and flexibility and swelling capacity of the prosthesis on the other hand. In one embodiment, the fibres are added to the hydrogel material in fine-cut form, preferably not exceeding 1 cm in length.

It is also possible to mix a foam with the hydrogel so as to make the hydrogel stronger, comparable to a fibre-reinforced hydrogel. Such a foam preferably has properties that correspond to those of Lycra. The foam that is used preferably has the following properties: a density of 20-80 kg/m$^3$, a tensile strength of more than 100 kPa, an elongation at break of more than 100%, compression resistance of 1.0-10.0 Kpa. The foam must be of medical quality, preferably of the type with open cells, and be reticulated, i.e. the cell walls between the individual cells have been removed.

It is also possible to pre-form the foam to the desired shape, for example in a mould, after which the hydrogel is formed in the mould (see Example 3).

Such foams and fibres exhibit a good absorption of the hydrogel material and accordingly they form a homogeneous mass. The foams and the fibres can be added to the monomer(s) from which the hydrogel is formed. Thus, said foams and/or fibres are present during the polymerisation process, as a result of which said foams and/or fibres become integrated in the hydrogel material. This makes the hydrogel tougher and tears will less easily form in the hydrogel material. Moreover, such foams and/or fibres exhibit a good adhesion to the hydrogel and a reduced risk of the hydrogel breaking or bulging out of the woven envelope.

In comparison with fine-cut fibres, a foam provides a more homogeneous distribution of the material, and consequently weaker spots will less easily be formed in the hydrogel, so that the extent of tear formation will be even less than when fibres are used.

The present prosthesis in particular comprises an envelope which is substantially made of fibres which are traction resistant. In the present description, The term "traction resistant fibre" as used in the present description is understood to mean a fibre which exhibits an elongation at break of at most 15%, preferably at most 5%.

The advantage of the use of such traction resistant fibres in the envelope is that this leads to a prosthesis having improved properties as regards fatigue resistance, durability and load-bearing properties.

The traction resistant fibres preferably have a tensile strength of at least 1 GPa, more preferably at least 3 GPa, even more preferably at least 5 GPa, in particular at least 7 GPa and more in particular at least 10 GPa. Thus, the best results are obtained as regards fatigue resistance and durability.

The fibres for the envelope preferably have an elasticity modulus of at least 50 GPa, preferably at least 75 GPa.

Examples of suitable fibres include, for example, Dyneema Purity®, which has a tensile strength of 3 GPa, an elasticity modulus of 98 GPa and an elongation at break of 3.4%.

The present prosthesis in particular comprises an envelope which is mainly made of fibres which are abrasion resistant. Abrasion is wear caused by shearing forces transversely to the direction of pulling. An abrasion resistant material does not wear easily upon contact and/or friction with other surfaces and retains its integrity. Said fibres will remain intact for a long period of time, therefore, in case they should grate along other surfaces, so that the risk of failure of the prosthesis is minimised. Fibres have a resistance of at least $10^4$ cycles, preferably at least $10^5$ cycles.

It is in particular preferable if the woven envelope for the present prosthesis is knitted or knotted, in particular knitted.

The size of the envelope is adapted to the application in question. In the case of a prosthesis for an intervertebral disc, the size of the envelope is comparable to the size of the natural intervertebral disc that is to be replaced.

This has the advantage that, in particular in the case of a knitted material, a structure having a suitable roughness is realised, so that there will be little migration, whilst furthermore an optimum bone adhesion will be obtained.

Preferably, polyethylene fibres are used in the woven envelope, which woven envelope in particular consists substantially entirely of such polyethylene fibres. Examples of suitable polyethylene fibres that are traction and abrasion resistant include, for example, Dyneema (brand) from DSM and the fibres described in WO 04/049980. It should be noted that the term "fibres" as used herein is also understood to refer to threads and yarns consisting of monofilaments or multifilaments. The thickness of the fibres is not bound by any limits and can be determined in dependence on the application by a person skilled in this field of the art.

In order to prevent the bulging out of the gel material even further, it is preferable to provide an additional protective layer under the woven envelope (i.e. between the woven envelope and the core), for example in the form of a membrane or a film. Such a protective layer envelopes the core entirely or partially. In the case of an artificial intervertebral disc, the core has the shape of a flattened body having an upper side and a bottom side, which upper side and bottom side are connected by a lateral surface. If the protective layer envelopes the core only partially, only the upper side and the bottom side, or only the lateral surface, will be enveloped, for example. The degree of enveloping by the protective layer will be selected in dependence on a number of factors, for example the mesh size of the woven envelope and the type of hydrogel material.

A membrane can be applied by folding a membrane around the core, for example. The membrane can be wound several times around the core, so that the core will be surrounded by, for example, two, four or even more membrane layers.

An example of a membrane that can be used in the present invention is the membrane Gore Preclude® It is a pericardial membrane consisting of expanded polytetrafluorethylene and has a thickness of 0.1 mm and a pore size of less than 1 .mu.m.

The aforesaid bulging out will be reduced even further as a result of the use of such an additional protective layer, because the small openings that may be present in the woven envelope are "closed" by the protective layer.

In particular a low degree of bulging out is obtained by using a dialysis membrane or other membrane or film having a pore size of about 1 nm 100 .mu.m as the protective layer. The pore size is suitably selected in dependence on, for example, the mesh size of the woven envelope and the type of hydrogel material.

If such a protective layer is used in prostheses comprising a wrapped envelope, a situation may occur under a load during use where the windings of fibres move apart, so that openings are formed. As a result, pressure will be exerted on the protective layer, possibly causing the protective layer and the gel material to bulge out. Since the protective layer is too weak to resist such a pressure, the protective layer might tear under pressure, which is undesirable. Consequently, the use of a protective layer, such as a membrane, with an envelope wrapped around said layer, does not suffice for being able to resist the required load in the case that a gel material is used as the core part.

The woven envelope according to the present invention preferably has a mesh size of at most 1 mm.sup.2. The term "mesh size" is understood to mean the size of the openings between the various yarns (fibres) of the woven material. If a mesh size exceeding this range is used, there will be an increased risk of the gel material bulging out. It is possible, however, to use a larger mesh size, possibly in combination with an extra protective layer. It will be apparent, however, that the mesh size depends both on the stitch density and on the thickness of the fibres that are used.

In a preferred embodiment, the knitted envelope has a stitch density of at least 15 stitches per inch (6 stitches per cm), preferably at least 20 stitches per inch (8 stitches per centimeter), and in particular at least 25 stitches per inch (10 stitches per centimeter), or even 50 stitches per inch (20 stitches per centimeter). If a smaller stitch density is used, the risk of bulging out of the gel material will be greater. It is possible, however, to use a smaller stitch density, possibly in combination with an additional protective layer. Different stitch densities may be used in the longitudinal direction and the transverse direction of the envelope.

The woven envelope may consist of one or more layers of a woven material, which layers are applied simultaneously or separately around the core. If the layers of the envelope are applied separately, the layers can be closed separately. If more than one layer is applied, it is of major importance that the dimensions of the various layers are correctly geared to each other, i.e. that the layers closely abut each other. After all, if one of the layers would be considerably smaller, this layer would bear the largest load, which is undesirable for reasons of overall strength.

Preferably, the woven envelope consists of at least two woven layers. In addition to that, other layers may be present. The warm layers may be identical or different from each other, for example as regards the fibre type, the fibre thickness, the coating, the mesh size and the like. Since the prosthesis comprises at least two layers, it has an enhanced level of safety in comparison with a single-layer envelope, since at least a second layer will remain to prevent the hydrogel from bulging out in case one layer is damaged. The prosthesis provided with an envelope consisting of at least two woven layers is furthermore capable of bearing a larger load. Since a prosthesis according to the present invention is safe, it is suitable for use as a prosthesis for a full intervertebral disc (nucleus and annulus).

In a preferred embodiment of the present invention, the at least two woven layers of the envelope are connected. By connecting the woven layers, the forces exerted on the envelope are distributed over the two woven layers, so that the layers of the prosthesis can bear the load proportionally. As a result, the stresses are homogeneously distributed over the various woven layers of the envelope, which is advantageous.

The individual woven layers can be formed by using different woven materials as layers or by wrapping a woven material made in one piece, for example a long tube (see hereinafter) several times around the core, as a result of which several layers are formed.

The (one or more layers of the) envelope can be provided in the form of a cylindrical woven material which is arranged around the core, after which the two open ends of the cylindrical woven material must be closed, for example by sewing.

It is also possible to apply a tubular woven material, which material is preferably arranged in a layer around the core, after which the tubular material is closed on an open side by turning, whereupon the tubular material is pulled back over the core in the reverse direction, thus applying a second layer—and possibly, by repeating the procedure, one or more further layers—of the envelope, which second layer is directly connected to the first layer, therefore, as a result of which the stresses are more homogeneously distributed over the various layers of the envelope.

In a preferred embodiment of the present invention, one or more layers are seamless. More in particular, all the layers present are seamless. The presence of a seam locally weakens a woven layer, which is rather less desirable. However, if more layers are present, with the seams located at different positions, there is a possibility that the presence of seams will not weaken the prosthesis. The absence of a seam leads to a stronger layer and thus to a stronger envelope. As a result, a layer will be damaged less easily when subjected to a load.

Preferably, a less flexible part is provided between the core and the envelope.

In another preferred embodiment of the present invention, the core has the shape of a flattened body having a lower and an upper side connected by a lateral surface. This is the shape of a disc or a flattened sphere, therefore. Such a shape is in particular optimal if the prosthesis is used as an artificial intervertebral disc, because the shape of the natural intervertebral disc is thus imitated. The shape of the core can be adapted according to the application in question.

In an embodiment in which the present core has the shape of a flattened sphere, anisotropic swelling of the core may occur, although the inventors do not wish to be bound by this theory. An increase in the size of the envelope is nearly impossible, but its shape can become rounder. A sphere has a higher volume/area ratio than a flat shape, so it is likely that the present prosthesis will exhibit relatively more axial swelling. This can also be advantageous in preventing the prosthesis from bulging out at the edges of the vertebrae.

In another embodiment, the present core has the shape of the natural intervertebral disc, i.e. one side is thicker than the other side (a so-called wedge shape). Furthermore, the present prosthesis, and thus the core and the part that may be less flexible, may be kidney-shaped, for example when used as a prosthesis for a lumbar intervertebral disc. The core might be shaped to follow the shape of the vertebra.

It is preferable if a less flexible part is present on one side or on both sides of the core. The advantage of this is that the prosthesis can be secured in the body by means of said less flexible part, for example to one or two vertebrae, between which the prosthesis is placed as an artificial intervertebral disc.

To ensure a good adhesion of the vertebrae to one or both sides of the prosthesis according to the invention used as an artificial intervertebral disc, it is preferable if the less flexible part is provided on at least one of the bottom side and/or the upper side of the core.

More in particular, the less flexible part serves as a so-called end plate. Such end plates are used for attaching the prosthesis to the surfaces of the vertebrae that face the intervertebral disc, so as to prevent the prosthesis from being displaced in the body upon being loaded. In one embodiment, such end plates are thin flexible plates, which are less flexible than the core, however.

After implantation, the thin flexible plates are pressed onto the adjacent bone under the pressure of the swollen or swelling core. The flexible plates are flexible enough to be able to practically follow the contours of the adjacent bone under said pressure. Since the flexible plates can assume the contours of the bone, the prosthesis is properly clamped between the adjacent bone parts. As a result, the risk of the prosthesis shifting relative to the adjacent vertebrae is small, if not altogether absent, which is necessary in order to realise a properly functioning prosthesis. Furthermore, said clamping fixation is advantageous because the good bone-prosthesis contact leads to a more proportional distribution of the forces over the bone when subjected to loads. This reduces the risk of damage or excessive wear on the bone and/or the prosthesis.

Such an end plate is provided in the woven envelope, as a result of which the woven envelope surrounds the gel material of the core as well as one or more end plates. As a result, a good bond between the end plates and the core material is obtained so as to prevent the end plate from becoming detached from the core material. Preferably, a flexible end plate is used.

Since the end plates are located within the envelope, a good and simple bond between the core and the end plate, a quick initial fixation can be realised without any contact area between envelope and bone being lost, so that a maximum area for bone ingrowth remains ensured as well.

In one embodiment of the present invention, a woven layer is first applied around a hydrogel core. Then a tubular woven material having a closed end is arranged around the core. Subsequently, a less flexible part, for example in the form of an end plate, having a central opening is moved over the tubular woven material. The tubular woven material is folded back so as to enclose the end plate in this way.

In one embodiment of the present invention, a tubular woven material having a closed-end is first arranged around the core. The tubular woven material is turned about its longitudinal axis and folded back. Then a less flexible part, for example in the form of an end plate, having a central opening is slid over the tubular woven material. The tubular woven material is folded back so as to enclose the end plate in this way.

If the less flexible parts have been arranged between two woven layers of the envelope, it is also possible, therefore, to use annular, less flexible parts provided with a central opening. Such an annular part (which part may also be kidney-shaped or oval with a central opening) is thus arranged on the second layer, whereupon the second woven layer is folded back through the opening of the annulus and possibly, after being folded back, attached to the second layer. As a result, the less flexible part is fixed in position in the prosthesis in that the second conveyor encloses the annulus in its entirety. Furthermore, a second less flexible part may be attached to the other side of the prosthesis in the same manner. In this case the folded-back part formed after the provision of the first flexible part is pulled through to the opposite side of the prosthesis. Then the second less flexible part is arranged on the folded-back part on the opposite side, whereupon the folded-back part is folded back through the central opening of the second part again. Subsequently the folded-back part can be attached to an underlying layer.

In a preferred embodiment of the present prosthesis, the envelope is provided with attachment materials. Said attachment materials may consist of a grid of metal or a plate provided with pins. Such attachment materials can be used in addition to or instead of end plates for securing the prosthesis in the body, for example to the vertebrae or other joints in which the prosthesis is implanted.

Attaching any connecting elements or attachment materials that may be present in the woven envelope is easier and more reliable than in a wrapped structure according to the prior art. A winding can shift relative to the other windings, and a connecting element can shift more easily along a winding. The consequence of this is that the risk of migration of the present prosthesis is reduced in comparison with prostheses implanted according to the prior art.

Preferably, the attachment materials comprise metal, and in particular they are made up of metal parts, for example of titanium or stainless steel. Such metal parts may be provided with a coating, if desired, such as a hydroxy-apatite coating, which stimulates bone adhesion and bone growth. The use of metal leads to a very strong and durable bond, which will remain intact also under a load.

In a preferred embodiment of the present invention, the fibres may be provided with a coating, if desired, such as a hydroxy-apatite coating, which stimulates bone adhesion and bone growth. Said coating is preferably applied only to the fibre parts that come into contact with the bone.

In a preferred embodiment, the attachment materials are selected from the group consisting of beads, clamps and nails and combinations thereof, which can be provided in or through the woven envelope and which can be attached to or inserted into the surface of, for example, the joint or the vertebra to which the prosthesis is to be attached. Said insertion into the adjacent bone material can also take place smoothly on account of the swelling force of the present prosthesis. If the present prosthesis, provided with a woven envelope provided with attachment materials, is implanted in the joint in partially or fully dehydrated condition, absorption of water will cause the prosthesis to swell in the body. As a result of said swelling pressure, the attachment materials, for example nails, will be forced into the adjacent bone material so as to realise a bonding attachment of the prosthesis thereto.

Such attachment materials can be provided both during the production of the woven envelope and after production, on the already completed prosthesis.

In the former case, beads and/or clamps, for example, are incorporated upon weaving, knitting, spool knitting, knotting, braiding, bobbin-lacing and the like. The advantage of this is that the attachment materials are integrated in the envelope and are thus undetachably connected to the woven envelope and to the prosthesis, therefore.

In the latter case, nails, for example, are provided through the already produced woven envelope. The advantage of this is that the woven envelope can be produced in a simpler manner, without using the nails, and that the nails are forced into the bone upon hydration of the core.

The selection of one of the two above techniques will depend on the individual circumstances.

The present invention further relates to a method wherein a core consisting of a gel material is provided with an envelope, characterised in that a woven envelope is provided.

The advantage of such a method is that the prosthesis obtained in this manner exhibits excellent properties as regards durability, implantability, fatigue properties and not bulging out.

Preferably, the woven envelope is produced separately from the core, after which the core is transferred to the envelope. The envelope is thus made by, for example, weaving, knitting or spool knitting, with the core being placed into the envelope thus formed, after which the envelope is closed.

In another preferred embodiment, the woven envelope is arranged around the core in situ. In this embodiment, the envelope is thus knitted, woven or spool-knitted around the core, for example, or the core is placed into the envelope halfway during said knitting, weaving or spoof-knitting, after which the envelope is completed. In general this makes it possible to realise a better fit between the core and the envelope.

In particular, the hydrogel is conditioned to a partially or completely dehydrated, or, in other words, not completely swollen state prior to being placed into the woven envelope. The advantage of this is that the partially or completely dehydrated hydrogel is less voluminous than the fully hydrated hydrogel and can thus be surgically implanted more easily, with minimal stretching of the ligaments and thus less complications after surgery and a less long rehabilitation period. The woven envelope is provided with a proper fit around the core of said partially or completely dehydrated or, in other words, not completely swollen hydrogel.

After implantation, absorption of the water present in the body will cause the hydrogel to hydrate and assume its final, fully hydrated form. In this fully hydrated form, it is preferable if the woven envelope is arranged around the hydrogel with a precise fit and is under tension so as to ensure an optimum strength, preferably assuming the shape of the cavity between the vertebra so as to obtain an optimum abutment with the vertebra. The present invention makes this possible because the hydrogel only hydrates after being implanted. In order to ensure that the woven envelope will fit around the hydrogel, it is preferable to check the size of the woven envelope in this saline solution which corresponds to the bodily fluid at the implantation site as regards molarity.

The present invention also relates to the use of the present prosthesis in replacing an intervertebral disc. Both the nucleus and the entire or partial annulus are removed in that case and replaced by the present prosthesis.

The present invention also relates to the use of the present prosthesis in replacing a nucleus of an intervertebral disc. In that case the nucleus is only removed from the annulus, and the present prosthesis is inserted into the remaining annulus.

Another application of the present prosthesis is the replacement of a meniscus in the knee.

The applications of the present invention are not limited to this, however; other applications are also possible, for example the replacement of cartilaginous tissue in general.

Further preferred embodiments of the present invention are defined in the claims. The preferences regarding the prosthesis also apply to the method, and vice versa.

The present invention will be explained in more detail hereinafter by means of a number of non-imitative examples. In the examples, three variables are used, viz. 1) the composition of the core material (silicone rubber or hydrogel material), 2) the traction resistance or non-traction resistance of the fibres used for the envelope, and 3) the manner in which the envelope is provided (wrapped or woven envelope).

The core material of the present invention is a gel material, preferably a hydrogel. In addition to that another, non-gel material, viz. silicone rubber is mentioned in the comparative examples.

In the comparative examples and the examples traction resistant or non-traction resistant fibres are used; the meaning of which terms has been described in the foregoing.

The last variable relates to the way in which the envelope is made, viz. whether it is a woven envelope or a wrapped envelope. In the case of a woven envelope, a distinction is made in the examples between a woven envelope and a knitted envelope.

COMPARATIVE EXAMPLE 1

A core of a hydrogel is wrapped in non-traction resistant fibres. This prosthesis is subjected to a number of tests, the result of which are shown in the table below.

COMPARATIVE EXAMPLE 2

A core of a silicone rubber material is wrapped in non-traction resistant fibres. This prosthesis is subjected to a number of tests, the result of which are shown in the table below.

COMPARATIVE EXAMPLE 3

A core of a hydrogel is enclosed in a woven envelope of non-traction resistant fibres. This prosthesis is subjected to a number of tests, the result of which are shown in the table below.

COMPARATIVE EXAMPLE 4

A core of a silicone rubber material is enclosed in a woven envelope of non-traction resistant fibres. This prosthesis is subjected to a number of tests, the result of which are shown in the table below.

COMPARATIVE EXAMPLE 5

A core of a hydrogel is wrapped in traction resistant fibres. This prosthesis is subjected to a number of tests, the result of which are shown in the table below.

COMPARATIVE EXAMPLE 6

A core of a silicone rubber material is wrapped in traction resistant fibres. This prosthesis is subjected to a number of tests, the result of which are shown in the table below.

COMPARATIVE EXAMPLE 7

A core of a silicone rubber material is enclosed in a woven envelope of traction resistant fibres. This prosthesis is subjected to a number of tests, the result of which are shown in the table below.

EXAMPLE 1

A core of a hydrogel is enclosed in a woven envelope of traction resistant fibres. This prosthesis is subjected to a number of tests, the result of which are shown in the table below.

EXAMPLE 2

A core of a hydrogel is enclosed in a knitted envelope of traction resistant fibres. This prosthesis is subjected to a number of tests, the result of which are shown in the table below.

COMPARATIVE EXAMPLE 3

The core consists of an ionized hydrogel. Four layers of Gore Preclude® (Gore Medical, USA) are arranged over said core, over which layers in turn a three-layer woven envelope is arranged. The woven envelope is a knitted envelope ("jacket") of Dyneema® fibres (DSM, Netherlands) having a pore size of less than 1 mm.

To produce the hydrogel, a gel mixture is first made of hydroxyethyl methacrylate (HEMA), sodium methacrylate (NaMA), distilled water, polyethyleen glycoldimethachylate 550 Mn (PEG2Ma crosslinker), and 2,2'-azobis-(2-methyl-propion-amidine)-dihydrochloride (polymerisation initiation agent). In mol proportions, the composition of the gel is HEMA (18 mol), NaMA (2 mol), $H_2O$ (79.93 mol), crosslinker (0.04 mol), polymerisation initiation agent (0.03 mol).

The mixture is prepared as follows. First NaMa is added to a measured amount of water and dissolved by stirring. Following that, HEMA, crosslinker and polymerisation initiation agent are added in steps, with stirring taking place after every addition. After the last addition, the entire mixture is stirred for one hour.

A pre-formed foam piece is placed in a cylindrical mould of 30.times.5 mm. The mixture is drawn into the mould, and thus into the pre-formed foam piece, by means of a vacuum. The mould is then placed in a water bath of 45.degree. C. In this way the gel is polymerised for one night. The polymerised gel is placed in a concentrated saline solution, so that monomers that remain are flushed and the gel is reduced in size as much as possible as a result of the saline solution drawing water from the gel through osmotic action.

The core of the present prosthesis is now formed by folding the membrane having a dimension of 12.times.12 cm over the gel in zigzag fashion, so that the gel is surrounded by four layers of membrane on all sides. Around this, the envelope, which has been knitted like a stocking, is applied by pulling the envelope over the core and turning the open side so that the open side is closed. The rest of the stocking is now folded back and arranged around the core again. This procedure is carried out once again and the last end is sewn closed with Dyneema® fibre. Stiffness is imparted to the prosthesis by placing it as a whole in a hypotonic saline solution, as a result of which the hydrogel will swell through osmotic absorption of water and the envelope will come under tension.

Tests

The following tests were carried out with the Comparative Examples and Example 1 and 2 and indicate to what extent the prosthesis have the required properties. The results of the tests are shown in Table 1.

A) The term "fatigue resistance" indicates to what extent the prosthesis is resistant to a large number of loads, and thus what will be the useful life of a prosthesis.

B) The term "ease of implantation" is understood to mean the simplicity with which the artificial intervertebral disc can be implanted by a surgeon during surgery. This characteristic depends on the size, the flexibility, the envelope and the swelling capacity of the prosthesis, among other factors.

C) The term "swelling capacity" is understood to mean the ability of the prosthesis to build up a high internal pressure on account of the water-absorption capacity of the core on the one hand and the stiffness of the envelope on the other hand.

D) The term "not bulging out" indicates the extent to which the core material will remain in the envelope upon being subjected to a load.

E) The term "abrasion properties" refers to the extent of wear caused by fibres rubbing along each other; a low extent of wear results in a high score as regards abrasion properties.

F) The term "bone adhesion" is understood to mean the ease and extent of adhesion of bone to the prosthesis in the body.

From Table 1 it also appears (see Comparative Example 5 and Comparative Example 1, for example) that the use of a woven envelop leads to improvements as regards bulging out and durability in comparison with a wrapped envelope.

From the above table it moreover appears (see for example Comparative Example 3 and Example 1) that the use of traction resistant fibres leads to improvements as regards fatigue and to abrasion properties in comparison with non-traction resistant fibres.

From the above table it appears (see Example 1 and Example 2) that the use of a knitted envelope provides better results as regards not bulging out and abrasion properties than the use of a woven envelope. An explanation for this might be that only one yarn is used in knitting while several yarns are used in weaving.

From the table it thus appears that a combination of aspects of the use of i) a gel material for the core part, ii) a woven material for the core envelope, and iii) a traction resistant fibre for the woven envelope in particular provides excellent properties as regards fatigue resistance, ease of implantation, swelling capacity, abrasion properties and not bulging out for the prosthesis according to the present invention.

TABLE 1

| Composition | Comp. Ex. 1 | Comp. Ex. 2 | Comp. Ex. 3 | Comp. Ex. 4 | Comp. Ex. 5 | Comp. Ex. 6 | Comp. Ex. 7 | Ex. 1 | Ex. 2 |
|---|---|---|---|---|---|---|---|---|---|
| core part | hydrogel | silicones | hydrogel | silicones | hydrogel | silicones | silicones | hydrogel | hydrogel |
| fibres | non-tr. resist. | non-tr. resist. | non-tr. resist. | non-tr. resist. | tr. resist. | tr. resist. | tr. resist. | tr. resist. | tr. resist. |
| envelope | wrapped | wrapped | woven | woven | wrapped | wrapped | woven | woven | woven |
| Property A | -- | - | -- | - | + | + | + | ++ | ++ |
| Property B | + | - | + | - | + | - | - | ++ | ++ |
| Property C | + | -- | + | -- | ++ | -- | -- | ++ | ++ |
| Property D | + | + | + | + | + | - | ++ | + | ++ |
| Property E | -- | - | - | - | + | + | + | + | ++ |
| Property F | - | - | o | -- | o/- | - | o | +/++ | ++ |

Explanation of signs: --very poor, - poor, o moderate, + good, ++ very good

The prosthesis according to Example 1 was tested under static and dynamic loads. Prior to said testing, the prosthesis, being in a dry state, was placed in a 0.15M NaCl water bath of 37.degree. C. to allow swelling under a load of 200N, an average load of a person in a reclined resting (steeping) position. For the static test, a prosthesis was compressed ten times to 15 kN, a load far in excess of the maximum load in the human body (viz. about 8 kN). The static load results are shown in FIG. 1. No damage to the prosthesis was observed. Any failure of the prosthesis is defined in a diagram as an abrupt force decrease at the same amount of stretch. This is not observed and thus failure does not occur.

Figure 2:
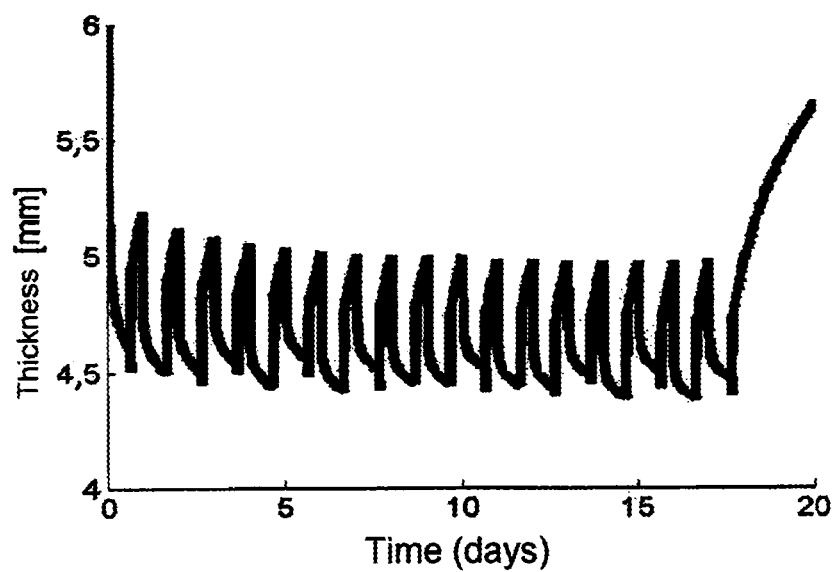
FIG. 2 shows the change in the thickness of a sample prosthesis during a fatigue test.

The prosthesis according to Example 3 was also subjected to a fatigue test (858 Mini Bionic II Test Systems MTS Systems Corporation, USA). During this test, the prosthesis was dynamically loaded with a load of 600-6000 N at a frequency of 10 Hz until failure or to a maximum of 10 million cycles. Because of the swelling and creep properties of the prosthesis, the prosthesis was loaded dynamically for 16 hours every day and statically, at 200 N, for 8 hours every day to allow recovery of the water content and to imitate the behaviour of an intervertebral disc in a body. After the 10 million cycles, the prosthesis could swell again under a load of 200N. Failure is defined as a decrease of at least 10% in the thickness of the prosthesis at the end of the compression or recovery phase (minimum and maximum thickness during the test) in relation to the comparable moment the previous day. FIG. 2, in which the thickness of the prosthesis is plotted against time, exhibits a decrease in the thickness of the prosthesis during the 16 hour compression phase and a recovery of the thickness during the recovery phase. After 10 million cycles, no damage to the prosthesis and no significant change in the dynamic behaviour of the prosthesis was observed.

Figure 3:
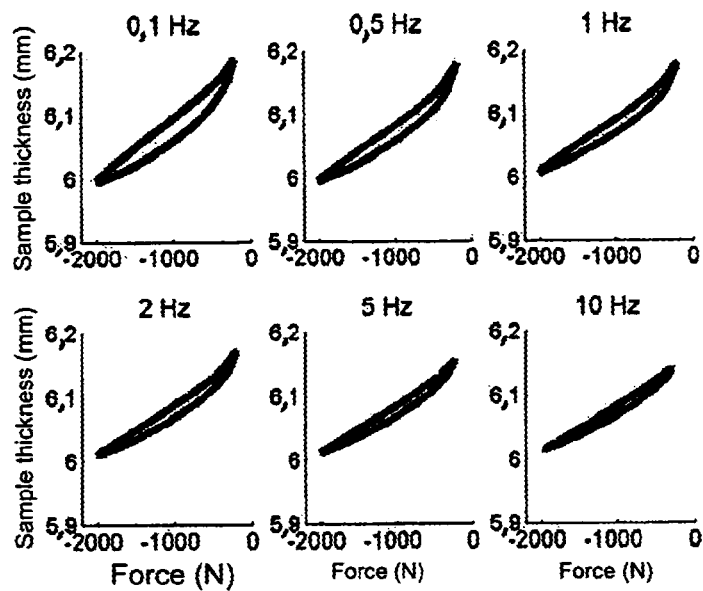
FIG. 3 shows the load on a present prosthesis while different frequencies are being used.

The influence of the frequency on the dynamic behaviour was also examined. The prosthesis according to Example 3 was to that end first subjected to a static load at 1100 N, at which creep took place. After equilibrium, the prosthesis was loaded between 0-2000 N at different frequencies. From FIG. 3 it can be derived that the present prosthesis exhibits typical viscoelastic behaviour. When the frequency increases, the viscous part becomes relatively smaller and the prosthesis starts to behave more elastically. During creep, water is squeezed out and the stiffness increases, as can be derived from FIG. 4.

Figure 4:
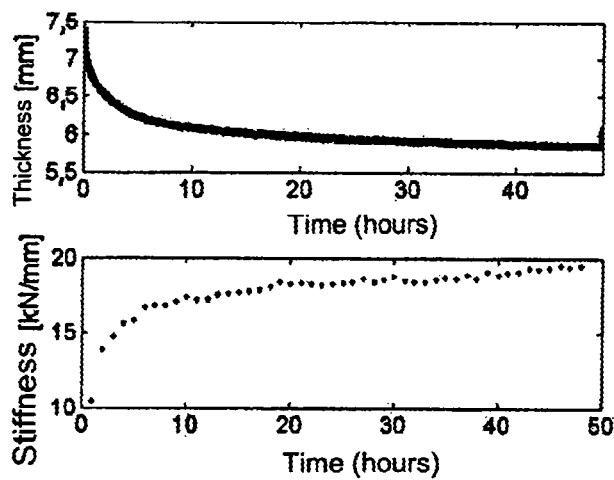
FIG. 4 shows the creep behaviour under a load of 1300 N of a prosthesis according to the present invention.

Furthermore, the stiffness during creep under 1300 N was measured. The prosthesis according to Example 3 was to that end dynamically loaded between 600-2000 N, at a frequency of 1 Hz, every hour during static load conditions under 1300 N. FIG. 4 shows that the thickness decreases during creep as a result of the outflow of water, and that the stiffness increases. Precisely as is the case with the intervertebral disc, the axial stiffness increases when the water content decreases.

The above results demonstrate that the present prosthesis exhibits behaviour comparable to that of the natural intervertebral disc and show that the prosthesis is strong and durable, so that one or more of the above objects of the present invention are thus accomplished. The stiffness of the prosthesis of Example 3 is in the order of 1-20 kN, which corresponds to the order of stiffness of the natural intervertebral disc, taking into account the relatively high load and small sizes that were used. The stiffness can also be compared to the hydrogel in itself, i.e. without envelope, when the gel can swell maximally. The modulus is 0.3 MPa and was measured by carrying out compression experiments in the same saline solution of 0.15 M. This means that by using an envelope as in this example, the stiffness of the entire prosthesis is at least a factor of 10 higher than when only a hydrogel is used.

The above static and dynamic tests demonstrate that the present prosthesis exhibits the same behaviour as the natural intervertebral disc and shows that the prosthesis is strong and durable, so that one or more of the above objects of the present invention are thus accomplished.

The invention claimed is:

1. A prosthesis comprising a core of a gel material and a fibre envelope which surrounds the core, wherein the fibre envelope consists of a woven material and comprises at least two layers of the woven material which are connected to one another and surround the core.

2. A prosthesis of claim 1, wherein the fibre envelope comprises traction-resistant fibres.

3. A prosthesis of claim 2, wherein the traction-resistant fibres have a tensile strength of at least 1 Gpa.

4. A prosthesis of claim 1, wherein the envelope comprises at least two or more layers of woven material.

5. The prosthesis of claim 1, wherein the envelope is knitted or knotted.

6. The prosthesis of claim 1, wherein the envelope has a mesh size of at most 1 mm$^2$.

7. The prosthesis of claim 5, wherein the envelope is knitted and has a stitch density of at least 10 stitches per inch (4 stitches per cm).

8. The prosthesis of claim 1, wherein the fibre envelope comprises polyethylene fibres.

9. The prosthesis of claim 1, wherein the gel material is a hydrogel.

10. The prosthesis of claim 9, wherein the hydrogel is reinforced with fibres having a tensile strength of at most 1 GPa.

11. The prosthesis of claim 9, wherein the hydrogel is reinforced with an amount of fibres of at least 5%, based on the weight of the hydrogel.

12. The prosthesis of claim 10, further comprising a protective layer present between the core and the envelope, which protective layer envelopes the core entirely or partial.

13. The prosthesis of claim 12, wherein the protective layer has pores having a pore size ranging between 1 nm and 100 μm.

14. The prosthesis of claim 1, wherein the stiffness of the prosthesis depends on the swelling pressure in the prosthesis, which is obtained by the balance between the swelling of the gel and the stiffness of the woven envelope, so that the fibres are biased and the amount of swelling is restricted.

15. A method for manufacturing the prosthesis of claim 1, wherein a core consisting of a gel material is provided with an envelope, wherein a woven envelope is provided.

16. The method of claim 15, wherein the woven envelope is produced separately from the core, after which the core is transferred thereto.

17. The method of claim 15, wherein the woven envelope is arranged around the core in situ.

18. The method of 16, wherein hydrogel is used as the gel material, which hydrogel is preferably placed in the envelope in a completely or partially dehydrated state.

19. A method for replacing an entire intervertebral disc, a nucleus of an intervertebral disc or a meniscus with a prosthesis comprising a core of a gel material and a fibre envelope which surrounds the core, wherein the fibre envelope consists of a woven material and comprises at least two layers of the woven material which are connected to one another.

* * * * *